United States Patent [19]

Günzler et al.

[11] Patent Number: 4,717,727
[45] Date of Patent: Jan. 5, 1988

[54] ESTERS OF PYRIDINE-2,4- AND 2,5-DICARBOXYLIC ACID AS MEDICAMENTS FOR THE INHIBITION OF PROLINE HYDROXYLASE AND LYSINE HYDROXYLASE

[75] Inventors: Volkmar Günzler, Bodenheim; Hartmut Hanauske-Abel, Dexheim; Jürgen Mohr, Bischofsheim; Georg Tschank, Mainz, all of Fed. Rep. of Germany; Kari Kivirikko, Oulu, Finland; Kari Majamaa, San Pedro, Calif.; Dietrich Brocks, Hünfelden, Fed. Rep. of Germany

[73] Assignee: Hoechst Aktiengesellschaft, Frankfurt, Fed. Rep. of Germany

[21] Appl. No.: 770,676

[22] Filed: Aug. 29, 1985

[30] Foreign Application Priority Data

Aug. 31, 1984 [DE] Fed. Rep. of Germany ....... 3432094

[51] Int. Cl.$^4$ .............................................. A61K 31/44
[52] U.S. Cl. .................................... 514/354; 514/801; 514/855
[58] Field of Search ..................... 514/354, 885, 801

[56] References Cited

U.S. PATENT DOCUMENTS 2,809,146 10/1957 Osborn et al. ...................... 514/190
2,852,519  9/1958 Kruse ................................... 546/170
4,457,936  7/1984 Draeger et al. ..................... 514/365

FOREIGN PATENT DOCUMENTS 3795 12/1965 France .
2123141 9/1972 France .

OTHER PUBLICATIONS

Burger's Medicinal Chemistry, 4th ed., Part II, Ed. by M. Wolff, pp. 1242–1244, 1978.
Muller et al., "Reversible Inhibition of ClQ Release from Guinea Pig Microphages by 2,2'-Dipyridyl".
Majamaa et al., "The 2-Oxoglutarate Binding Site of Prolyl 4-Hydroxylase.
Gunzler et al., "Influence of the Posttransitional Hydroxylation Step on the Secretion of Cl9, a Subcomponent of the First Component of a Complement by Macrophages".
Pliml, Synthetic Analogs of Curare Alkaloids, Chemical Abstracts 9665 f, 1955.

Primary Examiner—J. R. Brown
Assistant Examiner—John W. Rollins, Jr.
Attorney, Agent, or Firm—Finnegan, Henderson, Farabow, Garrett & Dunner

[57] ABSTRACT

Esters of pyridine-2,4- and -2,5-dicarboxylic acid act as inhibitors of proline hydroxylase and lysine hydroxylase and are suitable as fibrosuppressants and immunosuppressants, in particular for the treatment of disturbances of the metabolism of collagen and collagen-like substances and of the biosynthesis of $Cl_q$.

15 Claims, No Drawings

ESTERS OF PYRIDINE-2,4- AND 2,5-DICARBOXYLIC ACID AS MEDICAMENTS FOR THE INHIBITION OF PROLINE HYDROXYLASE AND LYSINE HYDROXYLASE

The invention relates to compounds of the formula I

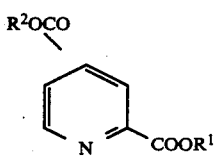

in which $R^1$ and $R^2$, which are identical or different, denote alkyl having 1 to 6 carbon atoms, but one of the radicals $R^1$ and $R^2$ can also represent hydrogen, the group $R^2OCO$ being bonded in the 4- or 5-position of the pyridine ring, for use as medicaments, in particular for the inhibition of proline hydroxylase and lysine hydroxylase as a fibrosuppressant and immunosuppressant. The invention also relates to medicaments which are composed of or contain a compound of the formula I. The invention also relates to the use of compounds of the formula I for the preparation of medicaments for affecting the metabolism of collagen and collagen-like substances and the biosynthesis of $C1_q$ and for the preparation of medicaments for the treatment of disturbances of metabolism of these molecules, and to processes for the preparation of medicaments for affecting the metabolism of collagen and collagen-like substances and the biosynthesis of $C1_q$.

Those compounds of the formula I which are preferred according to the invention are those in which both radicals $R^1$ and $R^2$ represent the alkyl radicals mentioned, preferably those having 1 to 3 carbon atoms, in particular ethyl.

It has been disclosed, in European patent No. B1 0,033,151 (U.S. Pat. No. 4,457,936), that carboxylic acids of hydroxyphenylthiazole and its derivatives affect collagen metabolism. These compounds act as inhibitors of proline hydroxylase and lysine hydroxylase and thus bring about a very selective inhibition of collagen biosynthesis by affecting the collagen-specific hydroxylation reactions. During the course of this, protein-bound proline or lysine is hydroxylated by the enzymes proline hydroxylase or lysine hydroxylase. If this reaction is suppressed by inhibitors then a collagen molecule which is incapable of functioning and is inadequately hydroxylated is produced, and this can be released from the cell into the extracellular space to only a small extent. In addition, the inadequately hydroxylated collagen cannot be incorporated in the collagen matrix, and it very readily undergoes proteolytic degradation. The consequence of these effects is an overall reduction in the amount of extracellular collagen deposits.

It is also known that the inhibition of proline hydroxylase, by known inhibitors such as $\alpha,\alpha'$-dipyridyl, leads to inhibition of $C1_q$ biosynthesis by macrophages (W. Müller et al., FEBS Lett. 90 (1978) 218; Immunobiology 155 (1978) 47). This results in loss of the classic pathway of complement activation. Thus inhibitors of proline hydroxylase also act as immunosuppressants, for example in immune complex diseases.

It is known that proline hydroxylase is effectively inhibited by pyridine-2,4- and -2,5-dicarboxylic acids (K. Majamaa et al., Eur. J. Biochem. 138 (1984) 239–245). However, in cell culture, these compounds are effective inhibitors only in very high concentrations (V. Günzler et al., Collagen and Related Research 3 (1983) 71). It has now been found, surprisingly, that esters of these compounds are highly active inhibitors of collagen biosynthesis in cell culture and organ culture.

The inhibitory effect of the substances on collagen biosynthesis can be demonstrated in cell culture using fibroblasts or other collagen-synthesizing cells or in organ culture of calvariae or other collagen-producing organs.

The inhibitory effect on $C1_q$ biosynthesis can be determined in cell culture using macrophages (Müller et al., FEBS Lett., loc. cit.).

The compounds of the formula I can be used as medicaments in the form of pharmaceutical products which contain them, where appropriate together with tolerated pharmaceutical vehicles. The compounds can be used as remedies, for example in the form of pharmaceutical products which contain these compounds mixed with an organic or inorganic pharmaceutical vehicle which is suitable for enteral, percutaneous or parenteral administration, such as, for example, water, gum arabic, gelatine, lactose, starch, magnesium stearate, talc, vegetable oils, polyalkylene glycols, vaseline, etc.

The pharmaceutical products can be in the solid form, for example as tablets, coated tablets, suppositories or capsules; in the semisolid form, for example as ointments, or in the liquid form, for example as solutions, suspensions or emulsions. Where appropriate, they are sterilized and/or contain auxiliaries, such as preservatives, stabilizers, wetting or emulsifying agents, salts to modify the osmotic pressure, or buffers. They can also contain other therapeutically active substances.

Compounds of the formula I can be used as insect repellents (U.S. Pat. No. 2,852,519) or as starting materials for bactericides (U.S. Pat. No. 2,809,146). They can be prepared by methods known from the literature, for example the process of U.S. Pat. No. 2,852,519.

Determination of the inhibitory effect is described below.

(a) Tissue of the EHS sarcoma tumor, which produces an extracellular matrix resembling basal membrane and produces, in particular, type IV collagen (Erkin et al., Exp. Med. 145 (1977) 204–220), is incubated in analogy to the method of K. Tryggvason et al. (Biochemistry 19 (1980) 1248–1289) in the presence of $^{14}$C-proline and of inhibitors in various concentrations. After the incubation has been stopped, the tissue is homogenized and extracted with dilute acetic acid. After NaCl precipitation, the extracted collagen was hydrolyzed with 6 M HCl, and the ratio of $^{14}$C-proline to $^{14}$C-hydroxyproline was determined.

(b) Isolated calvariae are incubated in analogy to the method of B. Peterkovsky and R. DiBlasio (Anal. Biochem. 66 (1975) 279–286) in the presence of U-$^{14}$C-proline and inhibitors. After the incubation has been stopped, the calvariae are homogenized, and the collagen is extracted with dilute acetic acid. After hydrolysis of the extract with 6 M HCl, the ratio of $^{14}$C-proline to $^{14}$C-hydroxyproline is determined. The following results were obtained:

Inhibitor of the formula I:

| $R^1 = R^2$ | Position of COOR$^2$ | Conc., μM | Inhibition, % |
|---|---|---|---|
| H | 4 | 670 | 50 |
| C$_2$H$_5$ | 4 | 3 | 50 |
| H | 5 | 2100 | 50 |
| C$_2$H$_5$ | 5 | 90 | 50 |

The compounds of formula I can be administered to patients in a dosage of 0.1 to 100 mg especially 0.5 to 10 mg per kg of body weight any day.

We claim:

1. A pharmaceutical preparation for inhibiting proline hydroxylase and lysine hydroxylase and for use as a fibrosuppressant and immunosuppressant which comprises an effective inhibiting or suppressing amount of a compound of the formula I

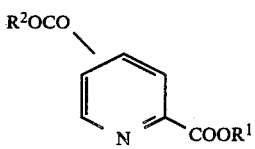

in which R$^1$ and R$^2$, which are identical or different, both are alkyl of 1 to 6 carbon atoms, or one of R$^1$ and R$^2$ is hydrogen and the other said alkyl, the group R$^2$OCO being bonded in the 4- or 5-position of the pyridine ring and a tolerated pharmaceutical vehicle.

2. A preparation as claimed in claim 1, in which both R$^1$ and R$^2$ are said alkyl.

3. A preparation as claimed in claim 2, in which R$^1$ and R$^2$ are alkyl of 1 to 3 carbon atoms.

4. A preparation as claimed in claim 3, in which R$^1$ and R$^2$ are ethyl.

5. A preparation as claimed in claim 3, in which R$^1$ and R$^2$ are methyl.

6. A method for affecting the metabolism of collagen and collagen-like substances and the biosynthesis of C1$_q$ which comprises administering to a patient suffering from disturbances of the metabolism of collagen and collagen-like substances and of the biosynthesis of C1$_q$ an effective amount of a compound of the formula I

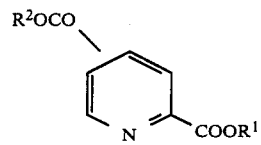

in which R$^1$ and R$^2$, which are identical or different, both are alkyl of 1 to 6 carbon atoms, or one of R$^1$ and R$^2$ is hydrogen and the other said alkyl, the group R$^2$OCO being bonded in the 4- or 5-position of the pyridine ring.

7. A method as claimed in claim 6, wherein in the compound of formula I R$^1$ and R$^2$ are said alkyl.

8. A method as claimed in claim 7, wherein said alkyl has 1 to 3 carbon atoms.

9. A method as claimed in claim 7, wherein R$^1$ and R$^2$ are ethyl.

10. A method as claimed in claim 7, wherein R$^1$ and R$^2$ are methyl.

11. A method for inhibiting proline hydroxylase and lysine hydroxylase and for treatment with a fibrosuppressant or immunosuppressant which comprises administering to a patient in need of such treatment an effective inhibiting or suppressing amount of a compound of the formula I

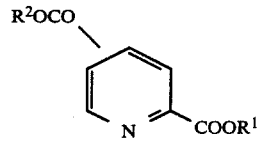

in which R$^1$ and R$^2$, which are identical and different, both are alkyl of 1 to 6 carbon atoms, or one of R$^1$ and R$^2$ is hydrogen and the other said alkyl, the group R$^2$OCO being bonded in the 4- or 5-position of the pyridine ring, together with a tolerated pharmaceutical vehicle.

12. A method as claimed in claim 11, in which both R$^1$ and R$^2$ of said compounds are said alkyl.

13. A method as claimed in claim 12, in which both R$^1$ and R$^2$ are alkyl of 1 to 3 carbon atoms.

14. A method as claimed in claim 13, in which R$^1$ and R$^2$ are ethyl.

15. A method as claimed in claim 13, in which R$^1$ and R$^2$ are methyl.

* * * * *